United States Patent
Lenigk et al.

(10) Patent No.: US 10,132,743 B2
(45) Date of Patent: Nov. 20, 2018

(54) FIXED OPTICS PHOTO-THERMAL SPECTROSCOPY READER AND METHOD OF USE

(71) Applicants: GENERAL ELECTRIC COMPANY, Schenectady, NY (US); TOKITAE LLC, Bellevue, WA (US)

(72) Inventors: Ralf Lenigk, Niskayuna, NY (US); Mark Marshall Meyers, Mechanicville, NY (US); Victor Petrovich Ostroverkhov, Ballston Lake, NY (US); Timothy Toepfer, Schenectady, NY (US); Keith Michael Looney, Glenmont, NY (US); Terry Lee Saunders, Clifton Park, NY (US); Kevin Paul Flood Nichols, Issaquah, WA (US); Matthew P. Horning, Redmond, WA (US); Benjamin K. Wilson, Kirkland, WA (US); Daniel Keith Connors, Maple Valley, WA (US); David Gasperino, Lake Forest Park, WA (US)

(73) Assignees: General Electric Company, Schenectady, NY (US); Tokitae LLC, Bellevue, WI (US)

( * ) Notice: Subject to any disclaimer, the term of this patent is extended or adjusted under 35 U.S.C. 154(b) by 18 days.

(21) Appl. No.: 15/217,493

(22) Filed: Jul. 22, 2016

(65) Prior Publication Data
US 2017/0211982 A1 Jul. 27, 2017

Related U.S. Application Data

(60) Provisional application No. 62/286,482, filed on Jan. 25, 2016.

(51) Int. Cl.
*G01N 21/17* (2006.01)
*G01N 25/00* (2006.01)

(52) U.S. Cl.
CPC .......... *G01N 21/171* (2013.01); *G01N 25/00* (2013.01); *G01N 2201/105* (2013.01)

(58) Field of Classification Search
CPC .................................................. G01N 21/171
See application file for complete search history.

(56) References Cited

U.S. PATENT DOCUMENTS

| 5,118,945 A | 6/1992 | Winschuh et al. |
| 7,036,979 B2 | 5/2006 | Mawatari |
| 8,111,399 B2 | 2/2012 | Rotter et al. |

(Continued)

FOREIGN PATENT DOCUMENTS

WO    2012031208 A2    3/2012

OTHER PUBLICATIONS

"The Endosafe—PTS™ ® Portable Test System User's Guide Version 7", Charles River, pp. 1-36, 2003.

(Continued)

*Primary Examiner* — Casey Bryant

(57) ABSTRACT

Disclosed is a low-cost, portable photo thermal spectroscopy (PTS) reader for use in detecting the presence of diseases in the bodily fluid of affected patients. The PTS reader is designed to be durable, easy to use and provide readings from the Lateral Flow Assay (LFA) with rapid results. Also provided are methods of use.

26 Claims, 9 Drawing Sheets

(56) References Cited

U.S. PATENT DOCUMENTS

| | | | |
|---|---|---|---|
| 9,091,594 B2 | 7/2015 | Furstenberg et al. | |
| 2001/0033381 A1 | 10/2001 | Stumbo et al. | |
| 2004/0180369 A1 | 9/2004 | Franzen et al. | |
| 2006/0240541 A1* | 10/2006 | Petruno | G01N 21/8483 435/287.2 |
| 2012/0062867 A1* | 3/2012 | Shibatani | G01C 3/085 356/4.01 |
| 2014/0377770 A1* | 12/2014 | Bischof | G01N 21/8483 435/7.1 |
| 2017/0234817 A1* | 8/2017 | Bischof | G01N 25/4806 435/7.1 |

OTHER PUBLICATIONS

Qin et al., "Significantly Improved Analytical Sensitivity of Lateral Flow Immunoassays by Using Thermal Contrast", Angewandte Chemie International Edition, vol. 51, Issue 18, pp. 4358-4361, Apr. 27, 2012.

Kim et al., "Molecular recognition using receptor-free nanomechanical infrared spectroscopy based on a quantum cascade laser", Scientific Reports 3, Article No. 1111, http://www.nature.com/articles/srep01111, Jan. 23, 2013.

International Search Report and Written Opinion issued in connection with corresponding PCT Application No. PCT/US2017/043217 dated Sep. 28, 2017.

* cited by examiner

FIXED OPTICS PHOTO-THERMAL SPECTROSCOPY READER AND METHOD OF USE

CROSS-REFERENCE TO RELATED APPLICATIONS

This application claims the benefit of U.S. provisional patent application 62/286,482 filed Jan. 25, 2016 and entitled "Integrated, Low Cost Photo-Thermal Spectroscopy Reader and Method of Use", the entire disclosure is incorporated herein by reference.

BACKGROUND

A typical RDT employs a dipstick or cassette format. A biological specimen (such as a blood) collected from a patient is applied to a sample pad on the test strip (or card) along with certain reagents. After a length of time (depending on the test), the presence of specific bands in the test strip (card) window indicates whether a certain antigen of interest is present in the patient's sample.

Typically, a drop of sample (e.g., blood) is added to the RDT through one hole (sample well), and then a number of drops of buffer are usually added through another hole (buffer well). The buffer carries the sample along the length of the RDT. In the currently marketed RDTs for malaria, hemoglobin present in red blood cells typically causes background residual background, which degrades the test. Lateral flow assays are an important tool in rapid diagnostic test (RDT). A rapid diagnostic test (RDT) is a medical diagnostic test that is quick and easy to perform. RDTs are suitable for preliminary or emergency medical screening, for use in medical facilities with limited resources, and offer a useful alternative to microscopy in situations where reliable microscopic diagnosis is not available or is not available right away. They also allow point-of-care (POC) testing in primary care in situations where formerly only a laboratory test could provide a diagnosis. RDTs do not require clinical diagnostic methods, such as enzyme-linked immunosorbent assay (ELISA) or polymerase chain reaction (PCR), can be performed independent of laboratory equipment by minimally trained personnel, and deliver instant results. RDTs provide results within two hours, and typically provide results in approximately 30 minutes.

However, to accomplish rapid diagnostic a reader and method is also required to perform analysis. In many situations the reader itself is expensive, requires maintenance and testing for quality control, and extensive operator training for accuracy. In certain areas, especially remote hospitals and third world countries, this is impractical. Thus, there is a need for a reader that is robust in these types of settings, low cost, portable, and is easy to maintain.

BRIEF DESCRIPTION

Disclosed is a low-cost, portable photo thermal spectroscopy (PTS) reader for use in detecting the presence of diseases in the bodily fluid of affected patients. The PTS reader is designed to be durable, easy to use and provide readings from the Lateral Flow Assay (LFA) within 1-6 minutes.

In certain embodiments a photo-thermal spectroscopy (PTS) reader for use with a lateral flow assay (LFA) analysis is provided. The PTS reader comprises a laser source configured to emit a laser beam having a wavelength of 400 to 900 nm, and a focusing lens positioned in front of the laser source and within the path of an emitted laser beam configured to focus the emitted laser beam. The reader also comprises a galvanometer having a mirror rotatable in the x-y directions to deflect the emitted laser beam, in an approximately downward direction, resulting in a laser beam path adjustable in the x-y position from the downward direction, a long wavelength infrared light (LWIR) detector array positioned outside the laser beam path and configured to capture thermal changes within the PTS reader. The components are encased in an optical bulkhead that has an opening positioned at its base to insert a LFA test strip under the deflected laser beam path. The PTS reader further comprises a microprocessor configured to operate the galvanometer and record thermal data received from the LWIR, a power source, and a passive thermal control to control temperature fluctuations of the PTS reader related to electrical operation.

Also disclosed are methods of use of the device with LFA.

DETAILED DESCRIPTION

The singular forms "a" "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least each numerical parameter should at least be construed in light of the number of reported significant digits and by applying ordinary rounding techniques.

In one aspect, provided is a low-cost, fixed optics portable photo thermal spectroscopy (PTS) reader for use in detecting the presence of diseases in the bodily fluid, such as but not limited to, blood, saliva, or urine, of affected patients. The PTS reader is designed to be easy to use and provide readings from a Lateral Flow Assay (LFA) which uses test strips (LFA test strips) for depositing a biological sample which, through lateral flow, separates and captures components of the sample for analysis. As used herein LFA may refer simply to the test strips. Typically, time to complete the assay read-out is within 10 minutes, in preferred embodiments, within 3 minutes. Read-out refers to testing from when the LFA test strip is inserted into the reader for analysis. In certain embodiments, the PTS reader is designed to be rugged and portable such that it can be used under a variety of environmental conditions, including wide ranges of temperature and humidity without extensive recalibration or set-up when moved.

While PTS readers for use with LFA test strips have been used, the design called for mechanical movement of the PTS optics using a mechanical translation stage. A similar design may employ movement of the LFA test strips in relationship to the optics. The mechanical movement, results in a scanning plan that typically involves 10 to 15 minutes depending on the test strip. Also, because mechanical movement is required, the moving parts may also require specific calibrations and maintenance related to alignment. As such, a PTS reader that moves the LFA test strips under an optical source, such as a laser, with a mechanical translation stage, takes additional time compared to an optically scanned system, and is more sensitive to thermal cross talk.

Figure 1A:
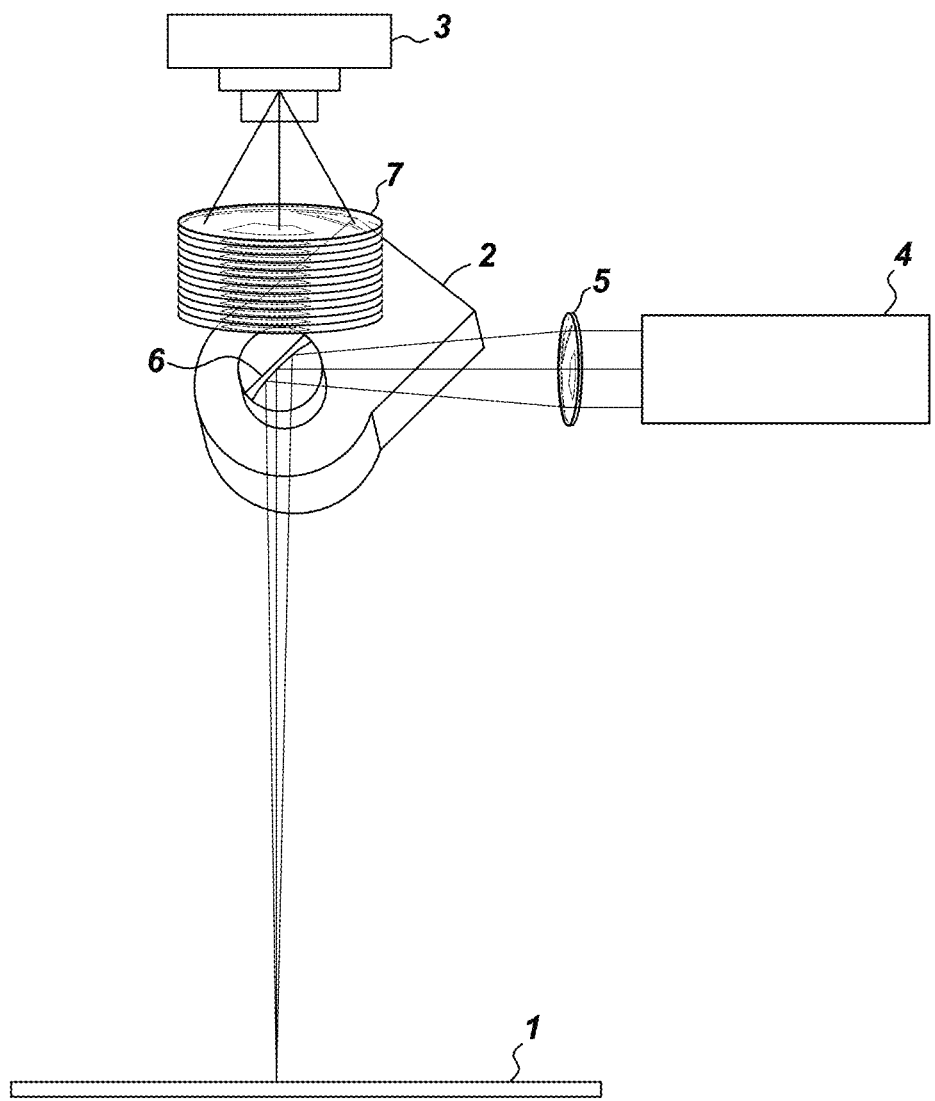
FIG. 1A is a diagram of an embodiment of the invention showing a PTS reader with a LWIR lens.
Figure 1B:
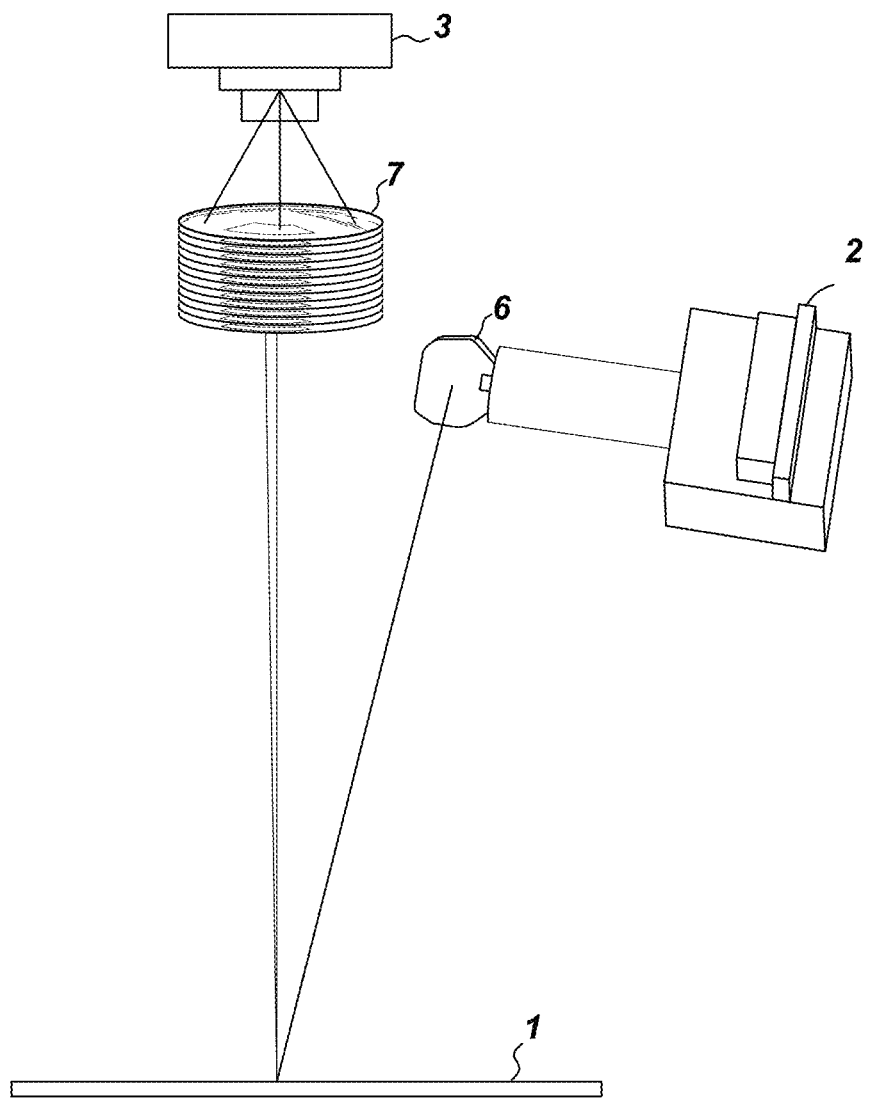
FIG. 1B is a diagram of the PTS reader in FIG. 1A showing a front view.

As shown in FIGS. 1A and 1B, in one embodiment, the fixed optics PTS reader is configured such that the LFA test strip (1) and the laser focusing optics are stationary; a laser spot is deflected over the surface of the test strip with a galvanometer (4). FIG. 1B is a front view of the reader shown in FIG. 1A.

As shown in the FIG. 1A and FIG. 1B, in certain embodiments, an infrared (IR) camera (3) monitors substantially the entire surface of the LFA test strip simultaneously as the imaged is focused through a IR objective lens (7) positioned in front of the camera. As such, the complete test strip may be monitored, edge to edge. In certain embodiments, where the test strip is non-uniformed or oversized, the monitoring may be greater than 90% or more of the surface area to account for the majority, if not all, of the testing surface.

As shown further in FIGS. 1A and 1B, in certain embodiments, the system is used with LFA which test for diseases based on antigens in the patient's blood. In one embodiment the laser focusing optics utilize a laser source (4) configured to emit a laser beam having a wavelength of 400 to 900 nm. In certain embodiments, the laser beam is passed through a focusing lens (5) positioned between the laser source and the galvanometer. The galvanometer has a mirror (6) which deflects the laser beam onto the surface of the LFA test strip.

In certain embodiments the laser source is a laser diode or diode-pumped solid-state (DPSS) laser; the laser configured to generate a pulsed focused laser-beam having a wavelength between approximately 400 nm and 900 nm.

In certain embodiments, the laser source is a DPSS laser emitting in the green (532 nm).

In certain preferred embodiments, a red laser diode is used, in order to avoid absorption from residual hemoglobin in the test strip. It is worth noting that by using a laser diode and not a DPSS (Diode Pumped Solid State) laser, cost savings can be achieved in the overall design of the device. Red laser diodes (640 nm) are low cost and compact, while DPSS tend to be higher performance, but much more expensive, reducing the affordability of the device in certain locations. In certain embodiments, the device further comprises an embedded microprocessor with software for instrument control, image capture and data analysis. In certain embodiments, the instrument controls may be accessible through a touch screen type of display with preconfigured demands and routines. As such a user, such as a medical technician in the field, may be trained and enabled to use the device with little intervention and with minimal training. The display may also be used for displaying test results. In certain embodiments, the reader may also be enabled to be connected to a network system for sharing results or to allow remote operations. The connection may be hardwired or wireless.

In certain embodiments, the instrument works by taking a biological sample from a patient and applying it to the LFA test strips. In certain embodiment the biological sample may include, but is not limited to, whole blood, serum, plasma, nasal secretions, sputum, urine, fecal matter, saliva, transdermal exudates, cerebrospinal fluid, and vaginal or urethral secretions.

In certain preferred embodiments, the biological sample is whole blood. In certain embodiments, within the LFA test strips, blood cells may be lysed to release any existing antigens into the buffer solution. If antigens are present in the blood, they are then conjugated to nanoparticles by targeted antibodies. The nanoparticles diffuse through the buffer solution and flow through to the test section of the LFA. The LFA substrate is patterned with anti-bodies which are specific to the disease being detected. In certain embodiments, the disease is malaria. If malaria antigens (or targeted proteins) are present in the buffer solution they will bind to the antibodies on the test strip. As the antigens are conjugated to nanoparticles, the test strip will capture the nanoparticles. As the nanoparticles absorb visible light and generate heat, the level of heat generated measurable and is proportional to the amount of disease antigen in the patient's blood.

In certain embodiment, an IR camera is utilized that is sensitive to long wavelength infrared light (LWIR) that is generated by objects whose temperatures are near room temperature, approximately 22° C. It should be noted calibration at higher or lower temperatures is also possible where the temperature is that of ambient conditions. By observing the LFA test strip with the IR camera, the invention can detect the presence of the disease marker by observing the increase in the temperature of the test strip. In certain embodiments, in order to keep the invention compact and low cost, the sensor may be an uncooled LWIR bolometer. In certain embodiments, the LWIR bolometers may be capable of detecting minor temperature differences, in a range favorable for identifying a disease marker. In certain embodiments, the temperature range may be approximately as small as 0.05° C. By observing the temperature distribution of the entire test strip with the LWIR camera, the concentration of nanoparticles, or the lack thereof, can be detected, which may be further indicative of the severity of the disease.

In certain embodiments, by generating test strips with multiple test regions, which incorporate different antibodies, multiple diseases, or multiple versions of the same disease can be detected with the same LFA and PTS reader system.

When a test strip is illuminated with laser light, the heat generated by the nanoparticles is conducted to the adjacent areas of the test strip. This heat will affect readings of the temperature of the adjacent regions of the test strip with a prior art PTS reader. As such, to overcome this deficiency, in certain embodiments, the method of using the device may comprise techniques for minimizing thermal cross talk. This is possible by having the PTS reader system comprise a scanning galvanometer mirror (galvo mirror or galvo) for the illumination, and an IR camera capable of monitoring the full temperature range of a positive test for the disease marker over the entire surface of the full test strip.

Figure 2:
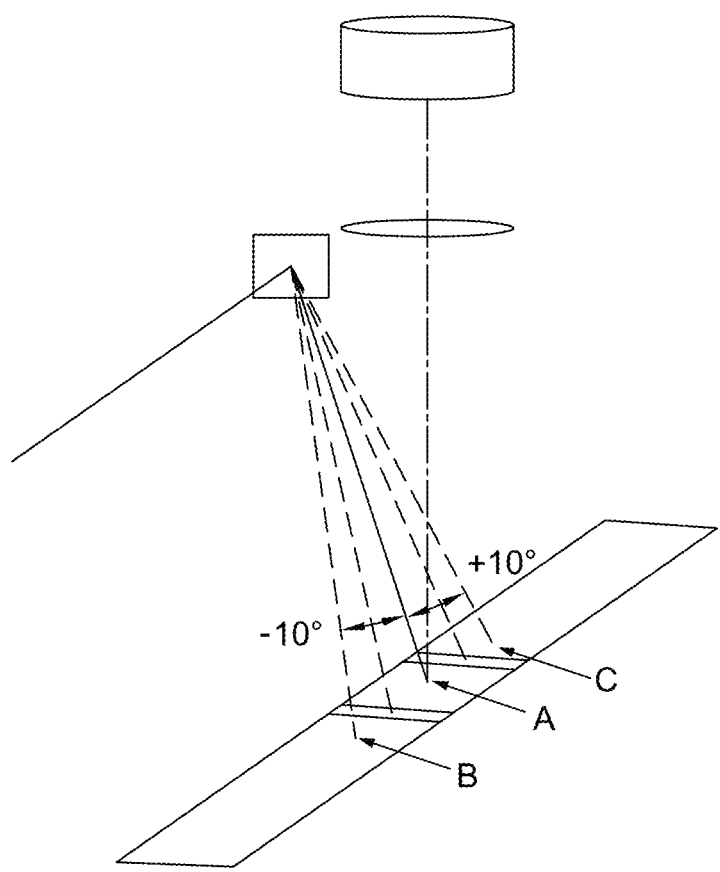
FIG. 2 is a diagram showing deflection of excitation illumination.

In certain embodiments, the scanning mirrors focuses the laser beam illumination to a specific area of the test strip for a short period of time (0.01-1 sec.) while the IR camera determines the local temperature. The heat generated in the illuminated test spot dissipates quickly; in certain embodiments heat dissipation is complete in 0.5-2 seconds. Thus, in certain embodiments, by deflecting the laser with the galvanometer to an area that is greater than 1 mm away from the last test point, the thermal cross talk from the last tested spot will be reduced and, in most cases eliminated. The laser beam can then be directed, by the scanning mirrors, to another test site that is beyond the thermal conduction region of the last test. A new test and subsequent tests thereafter may then be conducted. For example as shown in FIG. 2, the deflection of the laser beam is sufficient to illuminate specific areas of the LFA test strips to avoid cross talk and overlap illumination. In the example shown, deflection of the light path is controlled plus or minus 10 degrees in the plane tilted from the normal to the test strip surface as shown in the FIG. 2 to focus the beam anywhere between the center of the test strip (A) and as far as plus or minus 7 mm from the center point toward the ends of the strip (B and C), which can then be detected by the IR camera. The off axis illumination thus avoids interference with the light detector mount (lens and or camera) and provides for symmetrical scanning relative to the focusing point or optical axis. In most embodiments, larger rotation is possible to cover the entire surface of the LFA test strip. In certain embodiments, test strips can be 5 to 25 mm long, so that in certain embodiments, the configuration enables multiple tests to be made sequentially, without thermal cross talk and interference from the last tested spot. The use of scanning mirrors allows the test location to be changed in milliseconds rather than the seconds required using mechanical translation stages to move the test strip.

In certain embodiments, the LWIR camera may be positioned such that its optic axis is perpendicular to the plane of the LFA test strip, such that the entire strip area would be simultaneously in focus. As such, the different regions of interest, around the locations illuminated by the laser beam, may be imaged without the need to readjust the focus of the objective lens. In certain embodiments, the laser beam deflected down toward the sample strip may be positioned at a slight angle from normal, to the sample surface, to avoid obstructing the infrared light impingent upon the aperture of the infrared objective lens.

In certain embodiments, the tilt of the laser beam with respect to the sample normal may be chosen in the "roll" direction as referenced to the long dimension of the test strip; perpendicular to the strip long dimension. This orientation provides an advantage over an orientation with the tilt around the "pitch" axis as the distance between the galvo mirror and the laser spot on the sample changes less across the sample length. For example, in an embodiment with the galvo mirror positioned 40 mm above the sample surface and 7 mm away from the camera optic axis (the sample normal) in the "roll" direction (perpendicular to the sample's long axis), the galvo-to-sample beam propagation length at the center of the sample is approximately 40.6 mm, and at the edge of a 14 mm scan (7 mm from the scan center) it is approximately 41.2 mm, which is only about 0.6 mm longer.

In contrast, if the galvo is shifted by the same 7 mm but in the pitch direction (along the sample's long axis), the galvo-to-sample beam propagation length varies from 40 mm on one side to approximately 42.4 mm on the other side of a 14 mm scan, which is 2.4 mm change. For a focused laser beam, a change in the beam propagation will result in a change of beam spot, which in turn will result in a change in the photo-thermal heating efficiency. For a laser spot size of about 50 micrometers, a deviation of the beam propagation length by 0.6 mm will result in approximately 4% increase in beam area and decrease in optical power density, while for the 2.4 mm change, the spot area increase and power density reduction is approximately 38%.

To optimize the collection efficiency of the infrared objective lens, the camera sensor may be oriented such that the image of the sample strip is aligned along the diagonal of the sensor frame. This orientation enables capturing an image of the entire test strip with a greater optical magnification, resulting in less de-magnification, which may increase the effective numerical aperture (NA) of the system, and therefore increase photo-thermal signal captured by the camera.

In certain embodiments, the temperature data may be acquired in a form of a stream of digital image frames. Each frame may be configured as a 2D array of numbers representing local temperature across the area of the LFA test strip. Once the scan is complete, and the software receives and stores the data from the LWIR camera, an algorithm that is coordinated with the hardware data acquisition system may be applied to extract the line-scan data. For example a signal representing temperature along a line on the LFA test strip may be probed along which the nanoparticle distribution profile. This data may then be used to determine test outcome (e. g. generate a binary "positive/negative" result of the test). In certain embodiment, the method may comprise the acquisition of frames data, which is loaded to a processor and where the frames are cropped to only preserve relevant information within bounds of the LFA test strip area.

Figure 3:
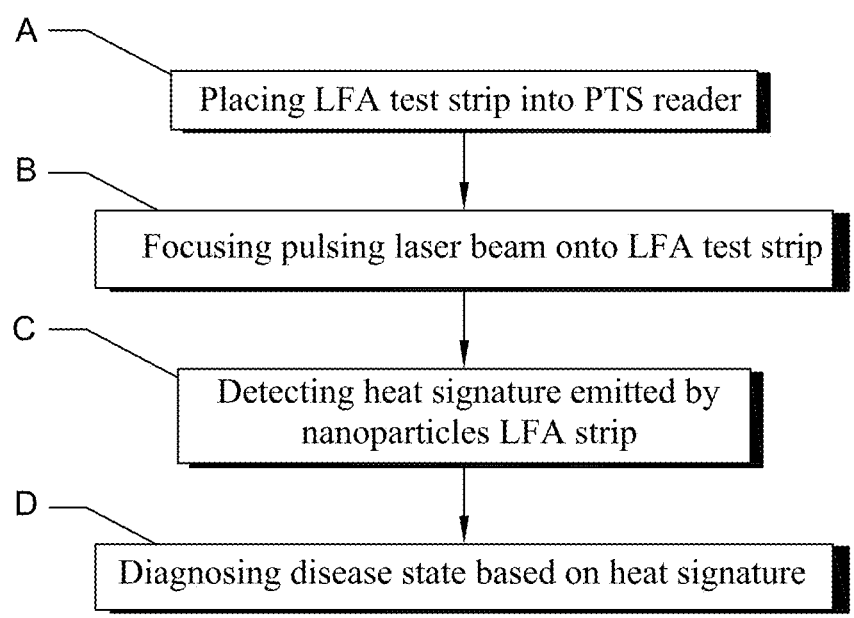
FIG. 3 is a representative method of analysis of a lateral flow assay (LFA) test strip containing a biological sample using the PTS reader.

As such, in certain embodiments, as shown in FIG. 3, a method of analysis of a lateral flow assay (LFA) test strip containing a biological sample may be accomplished by placing a lateral flow strip inoculated with a biological sample into a base opening of a photothermal spectroscopy (PTS) reader (step A) and subsequently pulsing a focused laser beam from the DPSS laser via the galvanometer onto the LFA test strip (step B). The LFA comprises test-lines having light absorbing bound nanoparticles to bind to targeted antibodies indicative of a disease state in the biological sample. By detecting a heat signature, emitted by the nanoparticles, with the LWIR detector (step C), a diagnosis of the disease state may be made.

The PTS reader used in the method shown in FIG. 3, comprises a laser source configured to emit a laser beam, and a focusing lens positioned in front of the laser and within the path of an emitted laser beam from the laser configured to focus the emitted laser beam. The PTS reader also comprise a galvanometer having a mirror rotatable in the x-y directions to deflect the emitted laser beam, passing through the focusing lens, in an approximately downward direction and where the deflected laser beam results in a laser beam path adjustable in the x-y position from the downward direction. A long wavelength infrared light (LWIR) detector array is also included and positioned outside the laser beam path to capture thermal changes within the PTS reader. The reader also has an optical bulkhead to encase the laser diode, the focusing lens, the galvanometer and the LWIR detector to maintain alignment of the emitted laser beam and the deflected laser beam path. An opening at the base of the bulk head allows for inserting a LFA test strip under the deflected laser beam path.

The PTS reader as described also comprises a microprocessor in communication with the galvanometer and LWIR detector to operate the galvanometer and record thermal data received from the LWIR detector. The microprocessor may be positioned within or outside the optical bulkhead. A power source for operating the laser diode, galvanometer, LWIR detector, and microprocessor may also be provided as well as a passive thermal control to control temperature fluctuations of the PTS reader related to electrical operation.

Figure 4:
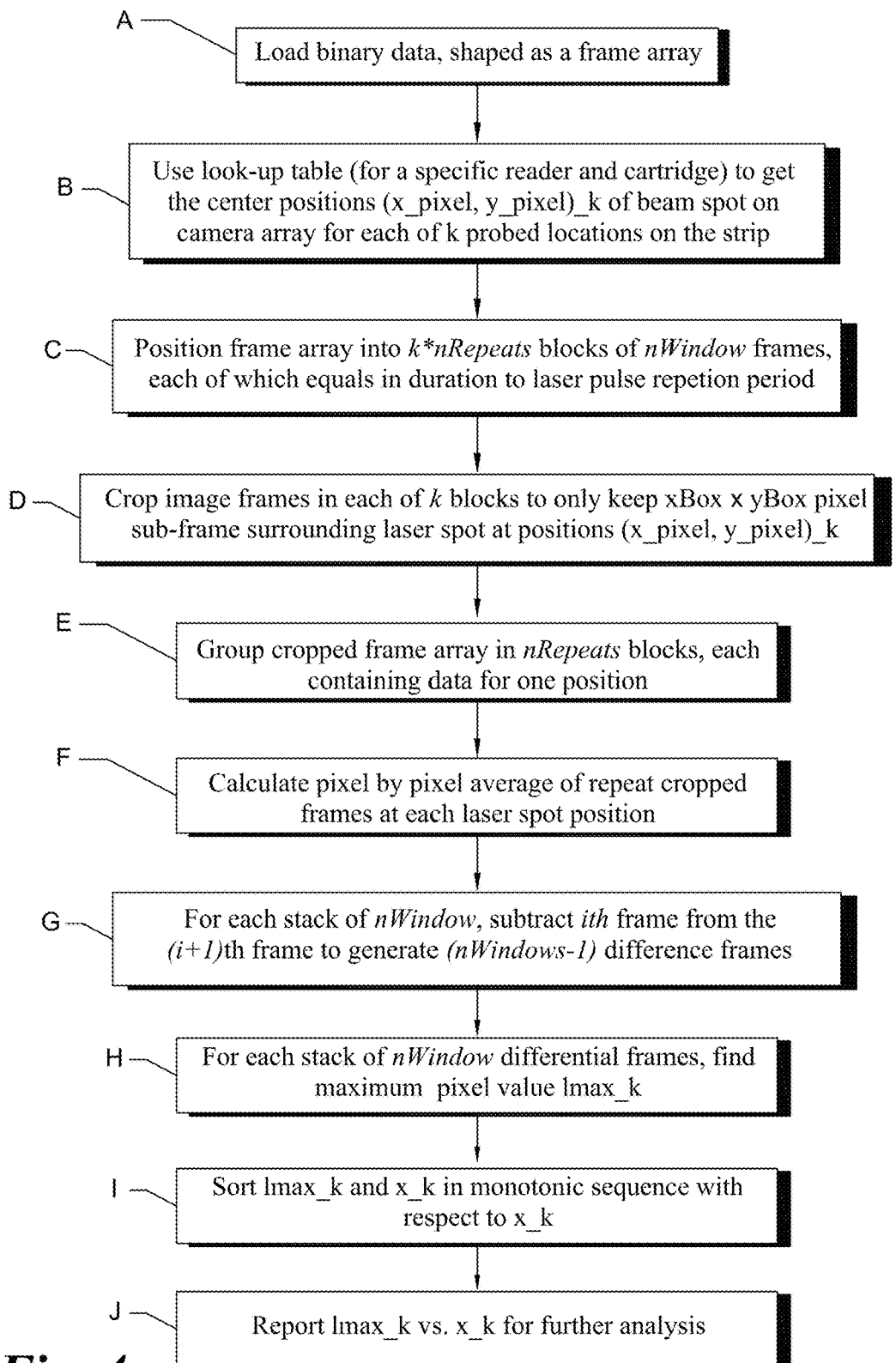
FIG. 4 is a representative workflow to allow rapid diagnosis.

A more detailed example of one such embodiment is shown in FIG. 4 which is a method to provide rapid and accurate detection over an entire surface of a LFA test strip. As shown in FIG. 4, image data may be converted into a line photo-thermal scan data. The data collected from the LWIR camera is loaded from the storage medium and logically divided into an array of individual frames (Step A). Next, a lookup table specifying the expected coordinates (x_pixel, y_pixel) of the laser spot on the camera sensor may be retrieved from permanent memory of the device or the processing computer (Step B). The lookup table may be unique for different type of the LFA supported by the device, with different strip dimensions and test line positions within the strip window. The type of the cartridge may be entered by the user or automatically determined by the reader via detection of a bar code, a digital image of the cartridge, or via other means. The lookup table may also be personalized to a specific reader unit or a group of units (for example, sharing the same hardware version) to account for potential alignment variability among units or design differences among hardware versions. Such personalized lookup tables can be generated in the production process via a calibration procedure. Next, the frame sequence is partitioned into sub-groups of nWindow frames that capture a time interval equal to the laser pulse repetition period, and are referred to as single-pulse sub-group or sequence (step C). Synchronizing laser pulsing with frame capture of the camera ensures that nWindow frames always capture the sample's photo-thermal response to one pulse, including at least one frame before exposure, and one or more frames during or after the exposure to the laser pulse. If the scan comprises k, where k represents spatial locations and the scan is repeated nRepeats times, the total number of single-pulse blocks will be k*nRepeats. In one embodiment, nWindow may be 5, k may be 100, and nRepeats between 2 and 10. For example if repeated 5 times, k*nRepeats would be 500, and the total number of captured frames would be nWindows*k*nRepeats=2500. Repeated scans may be used to improve the signal to noise ratio (SNR) of the photo-thermal image and in turn reduce the limit of detection of the analyte and improve disease detectability.

In certain embodiments, the frame data may be modified to eliminate changes in temperature profile not directly related to antibody detection. For example, in certain embodiments, the frame sequence is partitioned into short sub-groups, for example 5 sub-groups as shown, each of which captures temperature profile at times immediately before and after an individual laser pulse. In order to eliminate slow changes in the temperature profile, for example due to the gradual heating of the strip during the scan due to build-up of the deposited optical power, or slow temperature changes driven by evaporation of the liquid component flowing through the strip, a frame prior to the laser pulse is subtracted from the subsequent frames so that only fast change due to the laser pulse heating is captured.

In Step D of FIG. 4, a look-up table described in Step B, may be used to crop an image to select a smaller region of interest (ROI), for each sub-group of the pulses, around the spot where the strip was illuminated with the current pulse and a hot spot occurred. Since the position of the laser beam is deterministic, the ROI can be, for example, as small as 3×3 or 5×5 pixel (xBox multiplied by yBox pixels where the center pixel position is defined as x-pixel, y-pixel for the subgroup k), isolating only pixels most contributing to the heat generated by the current pulse. The choice of the ROI window size is dictated by the camera magnification and the pixel size as compared with the beam spot image size on the camera sensor, as well as the distance between the test spot and previous or subsequent test spot in the testing sequence. The ROI may be large enough to capture the temperature peak at the point being tested and small enough to exclude temperature from adjacent points.

In one embodiment, the thermal spot image size may be around 150 micrometers, and imaging magnification approximately 0.113. It results in the spot image of approximately 17 micrometers on the camera sensor, which in one embodiment may be approximately the size of the camera pixel. As the time following the spot exposure with the laser, the excess photo-induced heat dissipates into the surrounding material of the sample and results in the thermal image peak becoming broader in width and smaller in magnitude, and therefore choosing an ROI several pixels wide may preserve majority of the thermal peak shape and dynamics captured by the camera. On the other hand, if the previously exposed point in the scan is separated by about 2.5 mm (approximately 16 pixels in the present embodiment) from the current test point, the ROI excludes most of the pixels with residual heat from the previous scan point. Within the ROI, the magnitude of the generated heat, which in turn is related to the concentration of marker nanoparticles, may be extracted as a maximum pixel value, and average, or other more specialized methods such as a parameter of a functional fit.

In certain embodiments, each of the test locations is illuminated nRepeats times during the duration of the test and the resulting image is calculated as a pixel-by-pixel average of all nRepeats frames with the same timing with respect to the laser pulse.

As shown further in FIG. 4, in some embodiments, it may be beneficial to perform such averaging after cropping images to smaller areas surrounding the laser spot position (as described in Step D above). This may dramatically reduce the amount of data and accelerates analysis, which is especially important on small processor platforms. Thus in Step E, the frames that belong to the same spot position and time delay with respect to the laser pulse and were acquired in the repeat runs are grouped together, and a pixel by pixel average image is calculated for this position (Step F).

As the useful PTS signal originates from local change in the temperature due to the laser-induced heating, the first frame in the a single-pulse sequence of nWindow frames trimmed to the ROI as described above may be subtracted from the rest of the frames to eliminate static and slow-varying temperature patterns across the frame. Following the first frame subtraction, an absolute maximum across the rest of the frames within nWindow may be found and used as the photo-thermal response signal.

In a preferred embodiment as further shown in FIG. 4, the magnitude of the photo-thermal response may be determined as the maximum signal increase between any adjacent frames (frame (i+1) compared to frame i) within a given single-pulse sub-sequence. In such case, in Step G the adjacent (cropped and averaged) frames may be subtracted to produce I_(i+1)-I_i differential frame, followed by the maximum detection (max pixel value Imax_k) within the single-pulse differential frame sequence (Step H), which may be used as the photo-thermal response signal.

As the photothermal data were acquired in spatially non-sequential fashion, the data points may be sorted in the monotonic spatial order (increasing values of position coordinate x_k) for further processing or visualization (Step I), and be passed to the diagnostic decision algorithm or to a user for data visualization (Step J), which may be reported as Imax_k vs. x_k.

Figure 5:
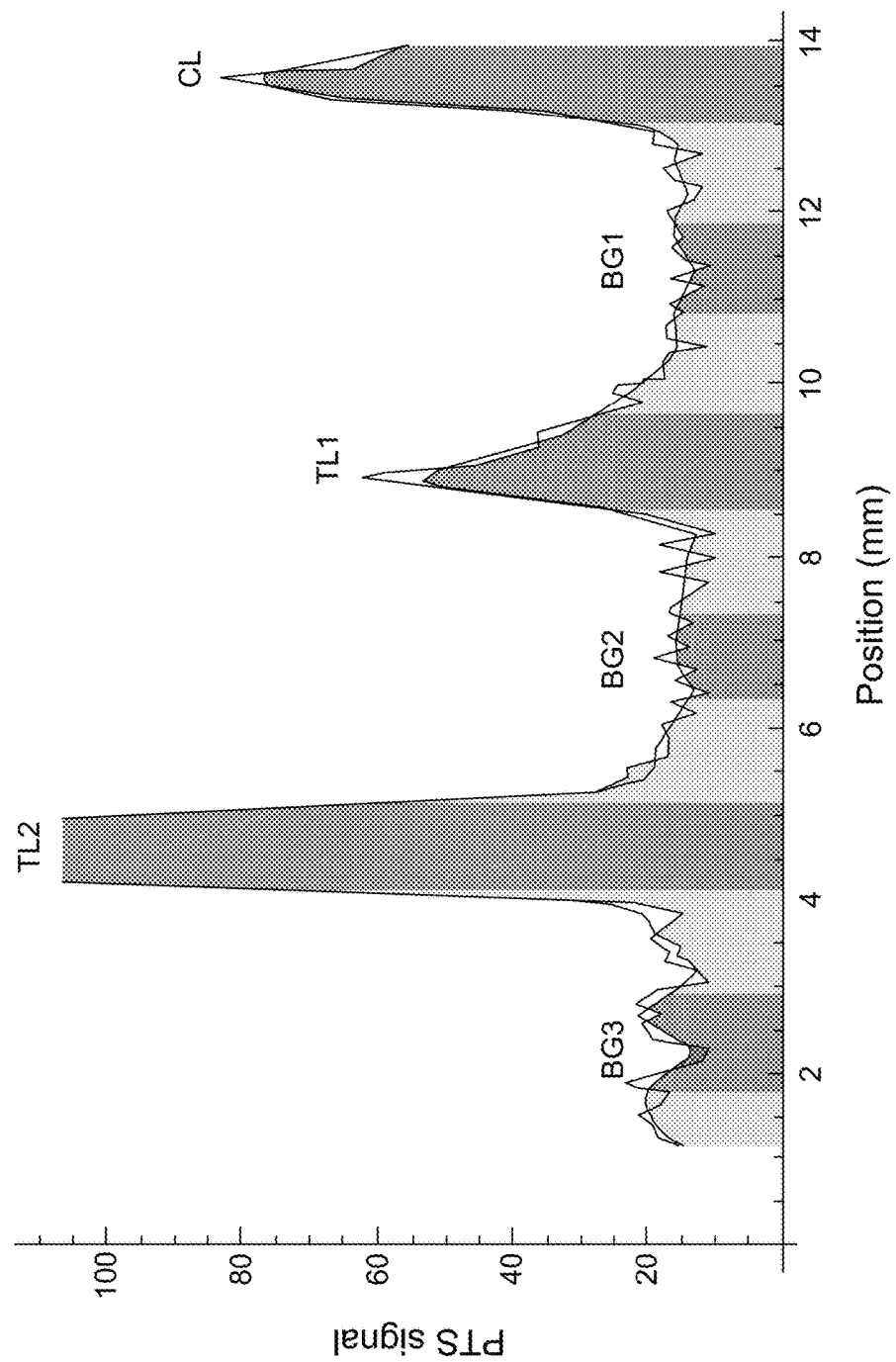
FIG. 5 is representative samples of testing of blood samples from malaria patients.

In certain embodiments, as the different locations are probed non-sequentially in space, the data points may be sorted to follow a monotonic spatial order, which may then be reported or displayed as a line scan profile. The line scans can be reported as a 2D plot of a curve as shown in FIG. 5. As shown the x axis in millimeters and is the relative position along the test strip. The y-axis is the relative intensity proportional to concentration of the nanoparticles captured on the test strip. The three peaks corresponds from left to right, test line 2 (TL2), test line 1 (TL1), and the control line (CL). The background related to thermal response is shown is designated as BG3-1).

The test outcome analysis may be performed on the line-scan profile. In certain embodiments, this may requires a-priori knowledge of the test strip geometry (e. g. approximate position of the control line, and the spacing between the control and test lines, as well as the nominal line thickness). Due to manufacturing variability in typical test strips, positions of the control and test lines may vary unit to unit or lot to lot. As the first step, a portion of the line scan (e. g. right-hand half of the scan in FIG. 5) may be analyzed to find the center of the control line, which can be done by nearest neighbor smoothing and looking for the maximum of the smooth curve. Alternatively, a centroid position may be calculated as shown in equation (1):

$$<x>=\text{sum}(x*\text{Intensity})/\text{sum}(\text{Intensity}) \quad \text{(equation 1)}.$$

Next, a section(s) of the scan at the expected position of the test line(s) is/are selected and mean value of the segments are calculated and compared to those of the "background" regions, which are section between lines where no intentional accumulation of nanoparticles is expected. Common statistical methods may be used to determine whether the test line value is significantly different from the background, which would simplistically constitute a "positive" reading of the test. More sophisticated methods may be applied to account for uneven background signal value, which may occur, for example, as a result of non-specific binding of nanoparticles or unintended non-homogeneities in the flow through the test strip.

Table 1 shows results of such described analysis as performed on the representative data from the scan in FIG. 5. Mean signal value over the designated segments comprising test and control lines on the strip as well as background signal between the lines is calculated. Statistical T-test can be used to calculate a p-score that estimates the probability of falsely rejecting the null hypothesis stating that the mean value of each of the line bands (Control, Test 1, and Test 2) be indistinguishable from the background bands surrounding each line (Background 1, 2, and 3) with alternate hypothesis assuming higher signal from the lines than the background. The binary diagnostic decision can be made by setting a probability score threshold (for example, the result is considered positive if p<0.05, and negative otherwise). Other ways of automatic quantification of the line intensity may be possible: the PTS score shown in Table 1 relies on estimation of signal and noise levels in different scan bands, and a positive test result may be established for the score exceeding a specific value (which may be determined using statistical hypothesis testing). In the example shown in FIG. 5 and Table 1, all three lines have a low p-score suggesting a valid result (positive control line), as well as a positive test for the two antibodies tested by Test Line 1 and 2. Similarly, the PTS scores are higher than the cut-off value of approximately 1, supporting the same interpretation.

TABLE 1

Test Result Statistical Analysis:

| Scan segment | Mean signal | p-score | PTS score |
|---|---|---|---|
| Control Line | 58.1 | 0.00016 | 23.2 |
| Background 1 | 14.6 | — | — |
| Test line 1 | 38.1 | 0.00006 | 13.3 |
| Background 2 | 14.8 | — | — |
| Test line 2 | 130.1 | 0.0003 | 38.1 |
| Background 3 | 17.7 | — | — |

Figure 6:
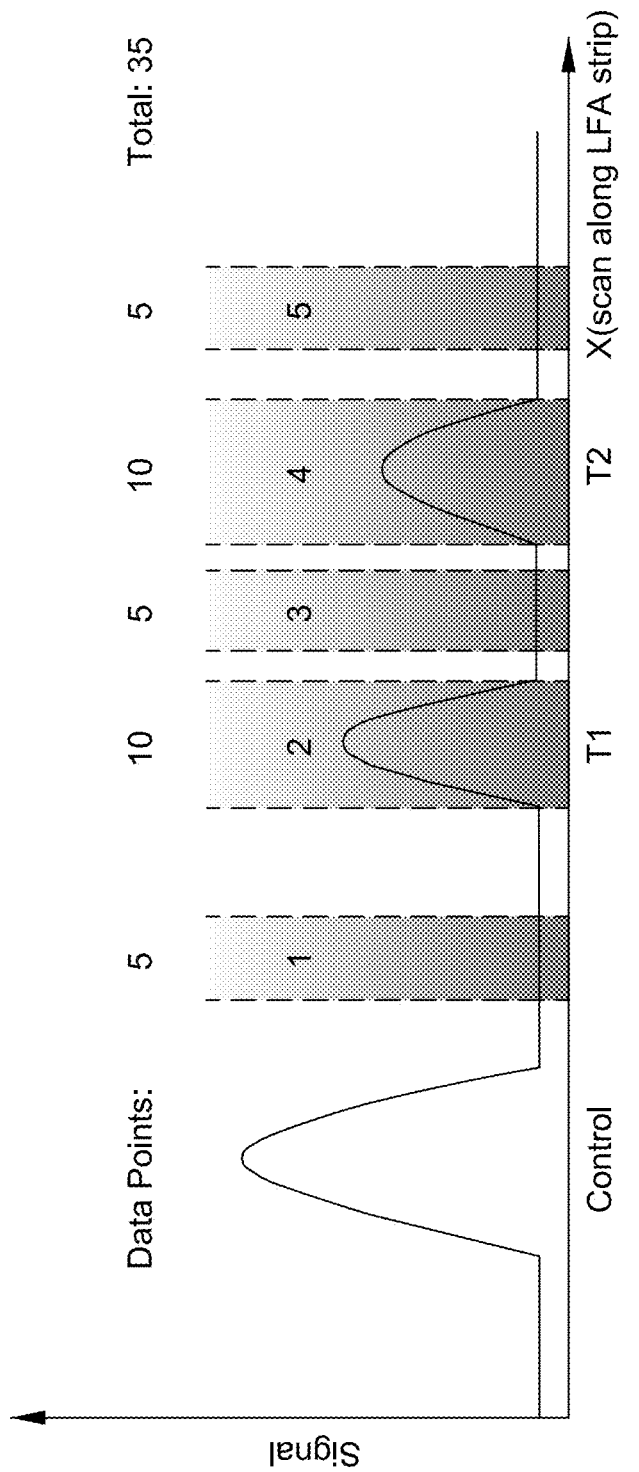
FIG. 6 is a diagram of adaptive scanning to reduce scan time by scanning selected areas.

In certain embodiments, the detection sensitivity and signal to noise ratio may be increased by scanning the test strip multiple times, and averaging over the scans. To compensate for the increase in total scan time, a method can be employed as shown in FIG. 6 ("Reducing scan time and adaptive scanning"). As a first step, one complete scan is performed to identify the presence and intensity of the control line by real-time analysis of the data. As the next step, the instrument scans selectively only in the areas that contain relevant information; for example areas designated 1 to 5 in FIG. 6. The designated areas would be scanned in subsequent rounds; scans 2 through 6 in Table 2 below. The positions are programmed in the instrument and are dependent on the test-strip that is analyzed, as different tests have different areas in which the test results will appear would also provide for a different number of data-points for each area; 35 in total as shown in FIG. 6. Thus, employing an adaptive scanning method allows real-time data analysis yet requires less scans where the signal is stronger. Thus, as is shown in FIG. 6, an initial scan, operating linearly, would require a total time of 2.5 to 6.5 minutes which may be reduced to a total scan time of between 1.33 to 2.66 minutes. The comparison is shown in Table 2.

TABLE 2

Reducing Scan Time Using Adaptive Scanning.

|  | Linear Scanning | Adaptive Scanning |
|---|---|---|
| Total Scan Time (min.) | 2.5-6.5 | 1.33- to 2.66 |
| Scan 1 Time (min.) | 1.5 | 1 |
| Scans 2-6 (min./scan) | 1 | 20 sec |
| Data points/scan | 100 | 35 |

Various embodiments of the laser beam deflection may be accomplished with a scanning mirror attached to a galvanometer, or a servo motor, or a low cost stepper motor with a gear head to increase its angular resolution.

Figure 7B:
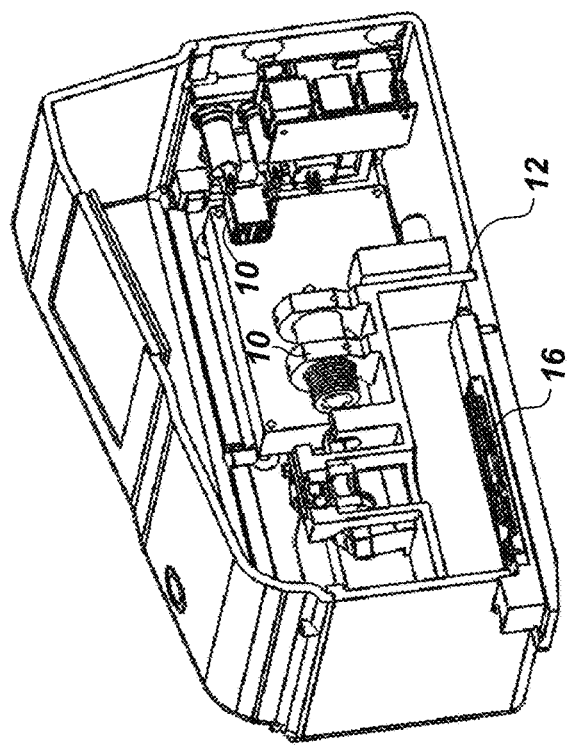
FIG. 7B is a cross section diagram of the PTS reader shown in FIG. 7A.
Figure 7A:
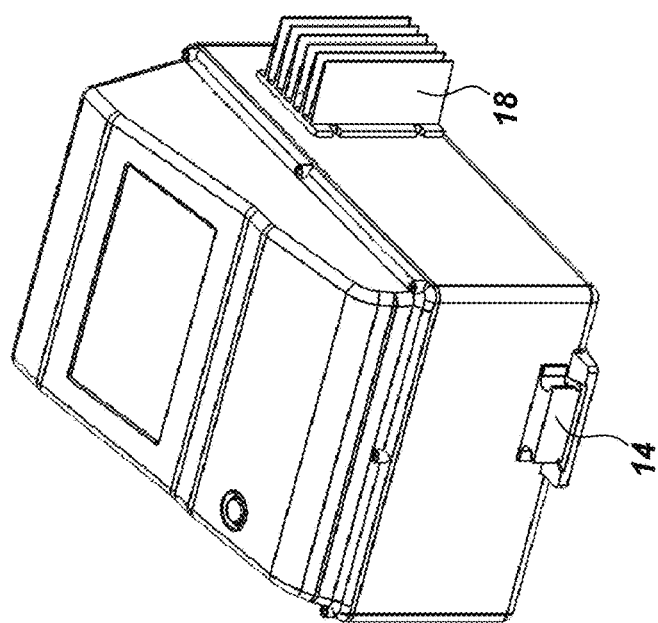
FIG. 7A is a diagram of an embodiment showing a PTS reader layout of optics and bulkhead component, top view

As such, as shown FIG. 7A has a top view and a cross-section view (FIG. 7B) of a representative PTS device. The device is designed to minimize thermal crosstalk from heat generated by the electronics by enclosing the electronic components (10) in an optical bulkhead (12) which reduces the amount of hot air reaching the test area. An LFA test strip

(16) may then be placed in the reader through an opening in the base (14). In certain embodiments, the device may be passively cooled by attaching heat generating electronics to heat sinks which have cooling fins (18) on the outside of the instrument's case. In still other embodiments, vented cooling fans may be used (not shown). This allows for passive cooling of the instrument and thermal management.

In certain embodiments, the device may be designed with sufficient passive cooling to maintain an internal temperature of the device, during operations, of less than 55° C., such that the software components and laser detection is improved. In certain embodiments, an externally vented heat sink may be attached to the galvanometer to enable passive heat dissipation from the bulkhead housing. It is worth noting that the bulkhead housing also may function as a shield from environmental factors including dust and other contaminants.

In certain embodiments, the use of nanoparticles in conjunction with the laser emitting in the red allows for the reduction in the effect of residual hemoglobin on the absorption of the test strip, due to hemoglobin's low absorbance in the red region, and prevents generating additional photothermal background that is not associated with antigen-conjugated nanoparticles and therefore only contributing to noise. It also allows for the use of red laser diodes, which are very robust and low cost due to their high volume manufacture for use in laser printers and DVD players. As such, in certain other embodiments, by utilizing nanoparticles whose absorption has been tuned to absorb in the red spectral region and using the red light to produce photothermal response, the sensitivity of the system to residual hemoglobin in the test strip may also be greatly reduced.

However, in another embodiment, the device may use green diode pumped solid-state lasers (DPSS), by modifying the LFA so as to not allow for the diffusion of hemoglobin onto the test strip area, or otherwise neutralizing natural absorbance of hemoglobin in the green part of the spectrum.

In certain embodiments, a method of use is provided which allows for the rapid detection of disease antigens and/or proteins generated by blood borne parasites, such as malaria in a low cost, portable instrument. This allows for use in remote areas where diseases such as malaria are present.

It is worth noting that by using a mirror based laser deflector, the device is capable of quickly testing the full length of a test strip without having to wait for the mechanical translation stages to move the test strip. This significantly decreases the time to complete the full test, and reduces wear of the system's mechanical components, as the only moving part is a robust galvanometer shaft with a light load of a mirror. Furthermore, the design provides for locating the laser beam with an adjustable mirror mounted on a galvanometer to different spots on the LFA test strip rather than moving the LFA test strip or the whole laser assembly.

In certain embodiments, the mirror based deflection may also allow for the avoidance of thermal cross talk by sampling the temperature of different areas of the test strip which are separated by >1 mm while the previously tested areas are cooling down.

In certain embodiments, a method is provided for reducing and limiting cross talk and involves illuminating one spot on the LFA test strip, and then moving the laser spot over a few mm to the next test position by deflecting it with the galvanometer. Moving a predefined distance, allows the heat contained within the previously tested spot to dissipate without affecting the reading at the next test position. In certain embodiments, heat generated takes about 1 second to dissipate, and the thermal dissipation occurs over 300-1000 μm length scales. By rapidly moving the test position over distances larger than 1 mm, the device avoids overlapping thermal readings. A high-density spatial sampling (with spatially adjacent points as close as 150 micrometers or less, for example) can still be achieved by increasing the time separation between the spatially adjacent test points and letting the earlier point to cool down completely while measurements are performed in other spatially remote locations on the test strip to reduce the overall scan time.

In certain embodiments, thermal imaging may be accomplished by using uncooled LWIR sensors to detect the temperature of the test strip. This avoids the much higher cost and size associated with the use of cooled IR cameras.

In certain embodiments, the combination of the components may allow for proper temperature control, positioning of the optics, and the decrease in testing time. In certain embodiments, the LFA test strip is not coupled to the galvanometer, but instead is merely positioned beneath it. For example, in certain embodiments, the galvanometer may be approximately 50 to 75 mm above the LFA test strip thus allowing the laser spot to be positioned anywhere along the 15 mm test strip by applying an analog control voltage to the galvo input. The deflector can traverse the full test strip-in less than a millisecond, which is much shorter than either the typical exposure time or the camera frame duration.

Thus, in certain embodiments provided is a low-cost, rugged, portable photothermal spectroscopy (PTS) reader that is designed for ease of use and provides rapid (sub 3-minutes) Lateral Flow Assay (LFA) analysis. The device comprises a stationary LFA test strip that is interrogated by a galvanometer, a scanning method that minimizes cross-talk between adjacent measurement spot, an optical bulkhead design minimizing thermal crosstalk from other components and environment, and a passive cooling system.

Figure 8:
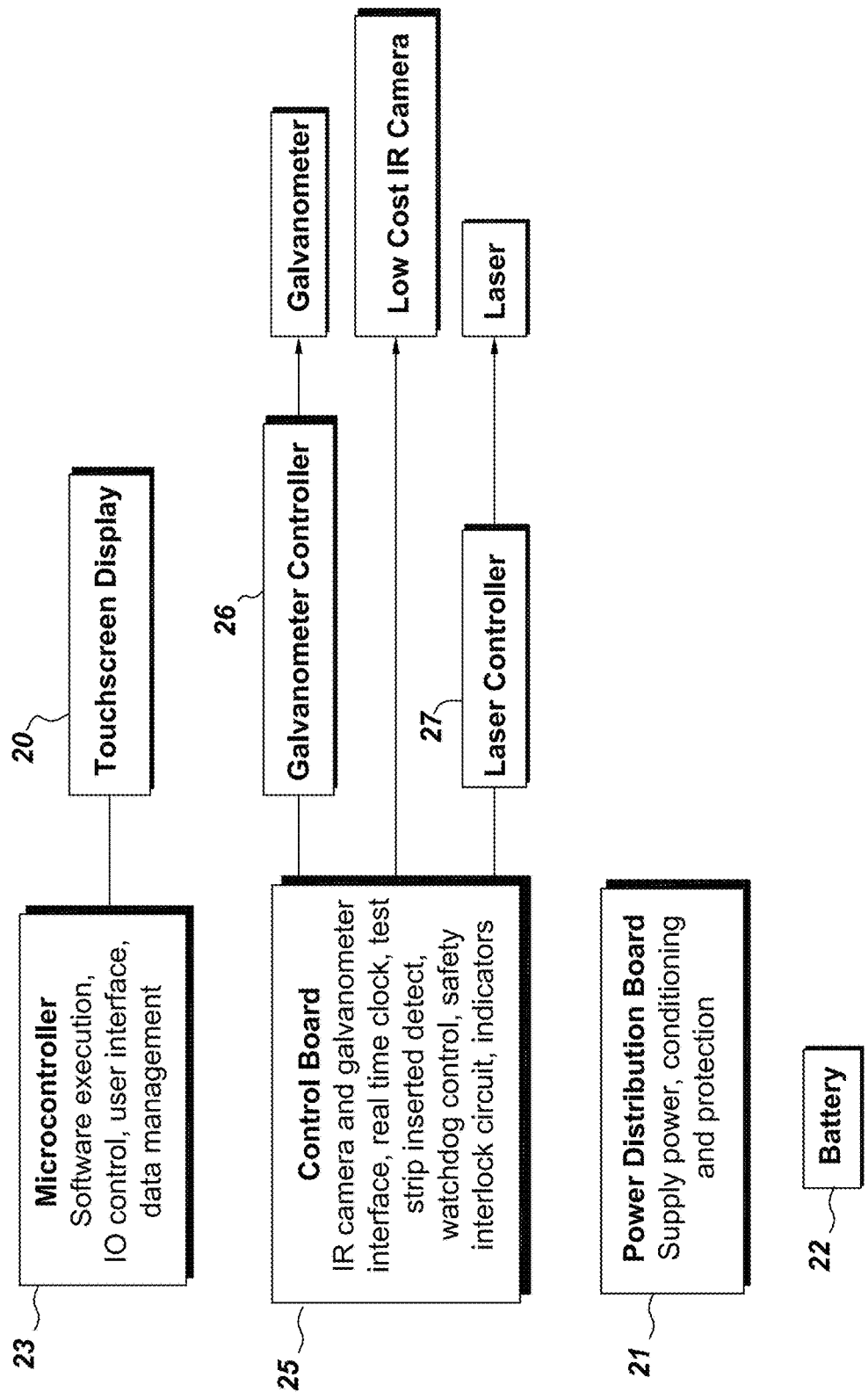
FIG. 8 is a diagram showing an embodiment of the communications of a PTS system.

As shown in the FIG. 8, diagram, in certain embodiments, the device also comprises features for durability and operation in tropical environment. These may include one or more features such as a user-interface (20) that allows users to be trained in minutes, a battery powered system with power management, such as a power distribution board (21) and a large capacity Li-Ion battery which may be rechargeable (22) (for example, 12 hour runtime), and a built-in microprocessor, which may also be referred to as a microcontroller (23). The microprocessor (23) may be configured with software enabling operations of the device. In certain embodiments the user-interface (20) may be a touch-screen for instrument control, data analysis and communication. In certain embodiments, the use of low-cost, low-power consumption components enables small form factor and long battery life. A control board (25) interfaced with the component of the PTS system provides for operations such as control of the galvanometer (26), laser operation (27), and an IR camera.

In certain embodiments, the reader operates by pulsing a focused laser-beam (diameter 50 μm to 1 mm) from a low-cost laser diode or DPSS laser (wavelength 400-900 nm) via a galvanometer onto LFA test-lines, where bound nanoparticles absorb the light. The heat signature emitted by the particles is then detected by an infrared-detector with focusing lens positioned directly above the LFA test strip. After reading out one spot, the galvanometer may move the beam to the next position, proceeding with an interstitial weaving pattern that minimizes thermal cross-talk between adjacent spots. In certain embodiments the interstitial weaving pattern is a serpentine pattern that moves across the surface of the LFA test strip. A microprocessor, which may be embedded in the reader, controls the entire instrument via software capable of performing the desired process. A simple, rugged user-interface consisting of a touch-screen, loading drawer for the LFA and on/off switches allows the user to be trained rapidly, within minutes. The system provides direct read-out of results, or can communicate them via a wireless network. The scanning time for a single LFA is less than 3 minutes. The resolution of the PTS reader system allows for semi-quantitative or quantitative determination of protein concentrations with appropriately designed tests.

In another embodiment, the PTS reader uses a low-cost x-y stage constructed from stepper motors in place of a galvanometer to control measurement spot positions. In a further embodiment, the PTS reader employs a laser line instead of a focused laser spot.

The invention claimed is:

1. A photo-thermal spectroscopy (PTS) reader for use with a lateral flow assay (LFA) analysis comprising:
   a laser source configured to emit a laser beam having a wavelength of 400 to 900 nm;
   a focusing lens positioned in front of the laser source and within the path of an emitted laser beam from the laser source, configured to focus the emitted laser beam;
   a galvanometer comprising a mirror rotatable in the x-y directions, to deflect the emitted laser beam, passing through the focusing lens, in an approximately downward direction and wherein the deflected laser beam results in a laser beam path adjustable in the x-y position from the downward direction;
   an optical bulkhead configured to;
   to encase the laser source, the focusing lens, the galvanometer and the LWIR detector to maintain alignment of the emitted laser beam and the deflected laser beam path; and
   having an opening positioned at its base to insert a LFA test strip under the deflected laser beam path;
   a long wavelength infrared light (LWIR) detector positioned outside the laser beam path, the LWIR detector captures thermal emission data and detects a heat signature from the LFA test strip, wherein the optical axis of the LWIR detector is perpendicular to a plane of the LFA test strip such that the entire LFA test strip is simultaneously in focus and the LWIR detector monitors substantially the entire surface of the LFA test strip simultaneously;
   a microprocessor in communication with the galvanometer and the LWIR detector and configured to operate the galvanometer and record thermal data received from the LWIR detector, the microprocessor is positioned within or outside the optical bulkhead;
   a power source for operating the laser source, galvanometer, LWIR detector, and microprocessor;
   a passive thermal control to control temperature fluctuations of the PTS reader related to electrical operation.

2. The reader of claim 1 wherein the power source is a lithium ion battery.

3. The reader of claim 1 wherein the microprocessor is capable of wireless communication.

4. The reader of claim 1 wherein the laser source is a laser diode or diode-pumped solid-state (DPSS) laser and is configured to generate a pulsed focused laser-beam having a wavelength between approximately 400 nm and 900 nm.

5. The reader of claim 4 wherein the laser diode is a red laser configured to generate a pulse laser-beam of approximately 640 nm.

6. The reader of claim 4 wherein the focused laser beam has a diameter between approximately 50 µm to 1 mm.

7. The reader of claim 1 wherein the passive temperature control comprises heat sinks attached to electronic components of the PTS reader, cooling fins located in the sides of the optical bulk head, vented cooling fans, an operating the laser source in a pulse sequence, or a combination thereof.

8. The reader of claim 7 wherein the passive temperature control is a heat sink.

9. The reader of claim 1 further comprising a user-interface in communication with the microprocessor configured to operate the PTS reader.

10. The reader of claim 9 wherein the user-interface is further configured to display at least one operating parameter of the galvanometer, at least one operating parameter of the LWIR detector, thermal data received from the LWIR detector, or a combination thereof.

11. The reader of claim 1 wherein the LWIR camera is positioned such that the LWIR camera optic axis is perpendicular to the plane of an inserted LFA test strip and the deflected laser beam is positioned at a slight angle from normal to the LFA test strip.

12. The reader of claim 11 wherein a sensor of the LWIR camera is positioned such that an image generated from the inserted LFA test strip is aligned along a diagonal of the sensor frame.

13. A method of analyzing a lateral flow assay (LFA) test strip containing a biological sample, the method comprising;
   placing a lateral flow strip inoculated with the biological sample into a base opening of a photothermal spectroscopy (PTS) reader, the PTS reader comprising;
   a laser source configured to emit a laser beam;
   a focusing lens positioned in front of the laser source and within the path of an emitted laser beam from the laser source configured to focus the emitted laser beam;
   a galvanometer comprising a mirror rotatable in the x-y directions to deflect the emitted laser beam, passing through the focusing lens, in an approximately downward direction and wherein the deflected laser beam results in a laser beam path adjustable in the x-y position from the downward direction;
   a long wavelength infrared light (LWIR) detector positioned outside the laser beam path and configured to capture thermal emission data from the LFA test strip within the PTS reader;
   an optical bulkhead configured to;
   to encase the laser source, the focusing lens, the galvanometer and the LWIR detector to maintain alignment of the emitted laser beam and the deflected laser beam path; and
   having an opening positioned at its base to insert the LFA test strip under the deflected laser beam path;
   a microprocessor in communication with the galvanometer and the LWIR detector and configured to operate the galvanometer and record thermal data received from the LWIR detector, the microprocessor is positioned within or outside the optical bulkhead;
   a power source for operating the laser source, galvanometer, LWIR detector, and microprocessor;
   a passive thermal control to control temperature fluctuations of the PTS reader related to electrical operation;
   pulsing a focused laser beam from the laser source via the galvanometer onto the LFA test strip where the LFA test strip comprises test-lines having light absorbing bound nanoparticles to bind to targeted antibodies indicitive of a disease state in the biological sample;

detecting a heat signature, emitted by the nanoparticles, by the LWIR detector; and adjusting the heat signature by:
  segmenting the LFA test strips into more than one image frame sections, where the frame section corresponds to frame images taken with the LWIR detector;
  detecting thermal data from each image frame during the pulsing step;
  processing the thermal data to retain data only within the LFA test strip area and its corresponding position on the LFA test strip;
  partitioning the retained data into frame sequences to create sub-groups where the sub-groups captures a temperature profile at times immediately before and after an individual laser pulse; and
  subtracting last frame, captured prior to the laser pulse, from the subsequent frames so that only fast change due to the laser pulse heating is captured.

14. The method of claim 13 where the laser beam is a pulsed focused laser beam having a wavelength between approximately 400 nm and 900 nm and has a diameter between approximately 50 µm to 1 mm.

15. The method of claim 14 wherein the laser source is a laser diode configured to generate a pulse laser-beam of approximately 640 nm.

16. The method of claim 14 where the laser beam path is moved across the surface of the LFA test strip by the galvanomter in an interstitial weaving pattern.

17. The method of claim 14 where the weaving pattern is restricted to areas comprising a test line.

18. The method of claim 13 where detecting the heat signature comprises; calculating thermal changes from a stream of digital image frames taken by the LWIR camera; transforming the thermal changes into line-scan data corresponding to nanoparticle distribution profile of the LFA test strip.

19. The method of claim 13 where the heat signature corresponds to the concentration of the targeted antibodies in the biological sample and is used to diagnosis the disease state.

20. The method of claim 13 where the laser beam path is non-sequential and the heat signature follows a monotonic spatial order.

21. The method of claim 13 where the heat signature is displayed as a line scan profile.

22. The method of claim 21 where the heat signature corresponds to the concentration of the targeted antibodies in the biological sample and is used to diagnose the disease state.

23. The method of claim 13 where the PTS reader further comprises a user-interface in communication with the microprocessor configured to operate the PTS reader and the user-interface displays at least one operating parameter of the galvanometer, at least one operating parameter of the LWIR detector, thermal data received from the LWIR detector, or a combination thereof.

24. The method of claim 13 where the biological sample is blood.

25. The method of claim 13 where the disease state is maleria.

26. A photo-thermal spectroscopy (PTS) reader for use with a lateral flow assay (LFA) analysis comprising:
  a laser source configured to emit a laser beam having a wavelength of 400 to 900 nm;
  a focusing lens positioned in front of the laser source and within the path of an emitted laser beam from the laser source, configured to focus the emitted laser beam;
  a galvanometer comprising a mirror rotatable in the x-y directions, to deflect the emitted laser beam, passing through the focusing lens, in an approximately downward direction and wherein the deflected laser beam results in a laser beam path adjustable in the x-y position from the downward direction;
  an optical bulkhead configured to encase the laser source, the focusing lens, the galvanometer and the LWIR detector to maintain alignment of the emitted laser beam and the deflected laser beam path, the optical bulkhead having an opening positioned at its base for inserting a LFA test strip under the deflected laser beam path;
  a long wavelength infrared light (LWIR) detector array positioned outside the laser beam path and configured to detect thermal emission data from the LFA test strip;
  a microprocessor in communication with the galvanometer and LWIR detector and configured to operate the galvanometer and record thermal data received from the LWIR detector as a heat signature, the microprocessor is positioned within or outside the optical bulkhead;
  a power source for operating the laser source, galvanometer, LWIR detector, and microprocessor;
  a passive thermal control to control temperature fluctuations of the PTS reader related to electrical operation,
  wherein the microprocessor is configured to execute instructions of adjusting the heat signature by:
    segmenting the LFA test strips into more than one image frame sections, where the frame section corresponds to frame images taken with the LWIR detector;
    detecting thermal data from each image frame during the pulsing step;
    processing the thermal data to retain data only within the LFA test strip area and its corresponding position on the LFA test strip;
    partitioning the retained data into frame sequences to create sub-groups where the sub-groups captures a temperature profile at times immediately before and after an individual laser pulse; and
    subtracting last frame, captured prior to the laser pulse, from the subsequent frames so that only fast change due to the laser pulse heating is captured.

* * * * *